US012773394B2

(12) United States Patent
Seet et al.

(10) Patent No.: US 12,773,394 B2
(45) Date of Patent: Oct. 27, 2026

(54) USE OF VALPROIC ACID FOR REDUCING POST-OPERATIVE SCARRING FOLLOWING A GLAUCOMA SURGERY

(71) Applicants: SANTEN PHARMACEUTICAL CO., LTD., Osaka (JP); SINGAPORE HEALTH SERVICES PTE LTD, Singapore (SG)

(72) Inventors: Li Fong Seet, Singapore (SG); Tina Tzee Ling Wong, Singapore (SG)

(73) Assignees: SANTEN PHARMACEUTICAL CO., LTD., Osaka (JP); SINGAPORE HEALTH SERVICES PTE LTD, Singapore (SG)

( * ) Notice: Subject to any disclaimer, the term of this patent is extended or adjusted under 35 U.S.C. 154(b) by 1032 days.

(21) Appl. No.: 17/783,185

(22) PCT Filed: Dec. 11, 2020

(86) PCT No.: PCT/SG2020/050740
§ 371 (c)(1),
(2) Date: Jun. 7, 2022

(87) PCT Pub. No.: WO2021/118469
PCT Pub. Date: Jun. 17, 2021

(65) Prior Publication Data

US 2023/0015595 A1 Jan. 19, 2023

(30) Foreign Application Priority Data

Dec. 11, 2019 (SG) ............................ 10201911970P

(51) Int. Cl.
*A61K 31/20* (2006.01)
*A61P 27/02* (2006.01)
*A61P 41/00* (2006.01)

(52) U.S. Cl.
CPC .............. *A61K 31/20* (2013.01); *A61P 27/02* (2018.01); *A61P 41/00* (2018.01)

(58) Field of Classification Search
CPC .............................. A61K 31/20; A61K 31/437
See application file for complete search history.

(56) References Cited

U.S. PATENT DOCUMENTS

2018/0369172 A1* 12/2018 Mohan ................. A61K 31/437

FOREIGN PATENT DOCUMENTS

WO WO-2012/021108 A1 2/2012

OTHER PUBLICATIONS

Seet et al., J. Mol. Med (2016)(94) ;; 321-334.*
Kent, Christopher; “Managing & Preventing Tube Shunt Problems”; Review of Ophthalmology; Jun. 8, 2015; pp. 1-15.
Extended European Search Report issued Nov. 24, 2023, in corresponding European Application No. 20899375.8; 12 pages.
Seet L. F. et al., Valproic acid suppresses collagen by selective regulation of Smads in conjunctival fibrosis. Journal of Molecular Medicine, Oct. 27, 2015, vol. 94, pp. 321-334 [Retrieved on Feb. 19, 2021] < DOI: 10.1007/S001 09-01 5-1 358-Z> pp. 321-324, 329; Fig. 6.
Chua J. et al., Valproic Acid Maintains Bleb Function Following Experimental Glaucoma Filtration Surgery in a Rabbit Model. Investigative Ophthalmology & Visual Science, Apr. 30, 2010, vol. 51, No. 13, p. 3198 [Retrieved on Feb. 19, 2021] < DOI: Notavailable> Whole document.
Seet L. F. et al., Valproic acid exerts specific cellular and molecular anti-inflammatory effects in post- operative conjunctiva. Journal of Molecular Medicine, Nov. 19, 2018, vol. 97, pp. 63-75 [Retrieved on Feb. 19, 2021] < DOI: 10.1007/S001 09-01 8-1 722-X> Whole document.
International Search Report and Written Opinion of the ISA issued in PCT/SG2020/050740, mailed Feb. 24, 2021; ISA/SG.
Li-Fong Seet et al.; “Effects of Valproic Acid and Mitomycin C Combination Therapy in a Rabbit Model of Minimally Invasive Glaucoma Surgery”; Translational Vision Science & Technolgy, vol. 11, No. 1, Article 30; Jan. 19, 2022; 15 pages.

* cited by examiner

*Primary Examiner* — Paul V Ward
(74) *Attorney, Agent, or Firm* — Harness, Dickey & Pierce, PLC

(57) ABSTRACT

The present invention relates to the use of valproic acid for reducing post-operative scarring following a glaucoma surgery. In one embodiment, the glaucoma surgery is glaucoma filtering surgery, which comprises creating a subconjunctival bleb. In another embodiment, the glaucoma surgery is minimally invasive glaucoma surgery (MIGS), which comprises implanting a glaucoma tube shunt under a subconjunctival space.

10 Claims, 11 Drawing Sheets

USE OF VALPROIC ACID FOR REDUCING POST-OPERATIVE SCARRING FOLLOWING A GLAUCOMA SURGERY

CROSS-REFERENCE TO RELATED APPLICATIONS

This application is a 371 U.S. National Phase of International Application No. PCT/SG2020/050740 filed on Dec. 11, 2020, which claims priority to Singapore Application No. 10201911970P filed on Dec. 11, 2019. The entire disclosures of the above applications are incorporated herein by reference.

TECHNICAL FIELD

The present invention relates to use of valproic acid in the treatment of glaucoma surgery.

BACKGROUND

Ocular surgeries involving the conjunctiva are frequently performed to delay progression of eye diseases, especially for glaucoma. Glaucoma surgery may be via conventional glaucoma filtration surgery (GFS) or minimally invasive glaucoma surgery, which is less invasive.

A common complication with glaucoma surgery is caused by post-operative ocular fibrosis. Indeed, the wound healing response to glaucoma surgery, regardless of conventional or minimally invasive form, involves inflammation and scarring as the final outcome. The formation of scars, composed mainly of disorganized collagen, necessarily disturbs conjunctival architecture which may then impair the biomechanical protective function of the postoperative conjunctiva, as well as disrupt normal blood/lymphatic vasculatures.

Currently, adjunct agents such as mitomycin C (MMC) are routinely applied to improve surgical outcome, mainly through reducing the amount of collagen being deposited in the scar. While these drugs are effective in preventing ocular fibrosis and improving the outcome of glaucoma surgery, they are known to cause sight-threatening complications including wide spread cell death, bleb leak, hypotony, and/or endophthalmitis.

Furthermore, as excessive or persistent inflammation after ocular surgery is associated with high risk of scarring, steroids as well as other anti-inflammatory drugs, are applied systemically, topically, or in the subconjunctiva, as post-operative management to prevent failure. However, these regimens commonly involve taking immunosuppressive/anti-inflammatory drugs for prolonged periods and steroids, in particular, are associated with potentially serious adverse effects.

There is therefore a need for an improved method of wound healing following glaucoma surgery.

SUMMARY OF THE INVENTION

The present invention seeks to address these problems, and/or provides an improved method of wound healing following glaucoma surgery.

According to a first aspect, the present invention provides use of valproic acid (VPA) in the manufacture of a medicament for preventing tissue degeneration following glaucoma surgery.

According to a particular aspect, the preventing tissue degeneration may comprise maintaining conjunctival collagen architecture.

The present invention also provides use of VPA in the manufacture of a medicament for maintaining a subconjunctival bleb formed in glaucoma surgery.

According to a particular aspect, the maintaining a subconjunctival bleb comprises maintaining conjunctival collagen architecture.

The VPA according to any aspect may comprise any suitable form of VPA. According to a particular aspect, the VPA may comprise a derivative, an analog, a salt, an ester thereof, or combinations thereof. For example, the VPA may comprise: sodium valproate, calcium valproate, valproate semisodium, divalproex, 2-n-propyl-3-aminopentanoic acid, 2-π-propyl-4-aminopentanoic acid, 2-n-propyl-4-hexynoic acid, or combinations thereof.

The glaucoma surgery may be any type of glaucoma surgery. According to a particular aspect, the glaucoma surgery may comprise creating a subconjunctival bleb. For example, the glaucoma surgery may comprise glaucoma filtering surgery or minimally invasive glaucoma surgery (MIGS). According to a particular aspect, the glaucoma surgery may be MIGS. In particular, the MIGS may comprise implanting a glaucoma tube shunt under a subconjunctival space. According to another particular aspect, the glaucoma surgery may comprise ab externo glaucoma surgery or ab interno glaucoma surgery.

The glaucoma surgery may comprise use of an anti-metabolite. The anti-metabolite may be any suitable anti-metabolite for the purposes of the present invention. For example, the anti-metabolite may be mitomycin C (MMC), 5-fluorouracil (5FU), or a combination thereof.

The anti-metabolite used in the glaucoma surgery may have a suitable concentration. According to a particular aspect, the concentration of the anti-metabolite as used in the glaucoma surgery may be ≤1.0 mg/mL.

The VPA may have any suitable concentration. For example, the VPA may have a concentration of 100-1000 μg/mL.

The medicament may be suitable for administration to a subject by any suitable means. For example, the medicament may be suitable for topical and/or subconjunctival administration.

The medicament may be suitable for administration at any suitable time. According to a particular aspect, the medicament may be suitable for administration immediately following the glaucoma surgery.

According to another particular aspect, the medicament may be suitable for administration for up to 6-120 months following the glaucoma surgery. In particular, the medicament may be suitable for administration daily for at least 12 weeks following the glaucoma surgery.

The present invention also provides a use of valproic acid (VPA) in the manufacture of a medicament for forming a weak subconjunctival scar following glaucoma surgery. The glaucoma surgery may be as defined above. In particular, the glaucoma surgery may comprise implanting a glaucoma tube shunt under a subconjunctival space.

According to a particular aspect, the forming a weak subconjunctival scar may comprise preventing encapsulation of the glaucoma tube shunt by collagen fibers. According to another particular aspect, the forming a weak subconjunctival scar may enable the glaucoma tube shunt to maintain its aqueous outflow ability through a lumen thereof.

There is also provided a use of valproic acid (VPA) in the manufacture of a medicament for preventing encapsulation of a glaucoma tube shunt implanted under a subconjunctival space.

Another aspect of the present invention is a use of valproic acid (VPA) in the manufacture of a medicament for maintaining aqueous outflow ability of a glaucoma tube through a lumen thereof after the tube is implanted under a subconjunctival space.

The glaucoma surgery may comprise use of an anti-metabolite. The anti-metabolite may be any suitable anti-metabolite. For example, the anti-metabolite may be, but not limited to, mitomycin C (MMC), 5-fluorouracil (5FU), or a combination thereof. The anti-metabolite may have a suitable concentration. According to a particular aspect, the anti-metabolite may have a concentration of 1.0 mg/mL.

According to a particular aspect, the medicament may further comprise an anti-metabolite. The anti-metabolite may be as described above.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings. In the drawings.

DETAILED DESCRIPTION

Figure 1:
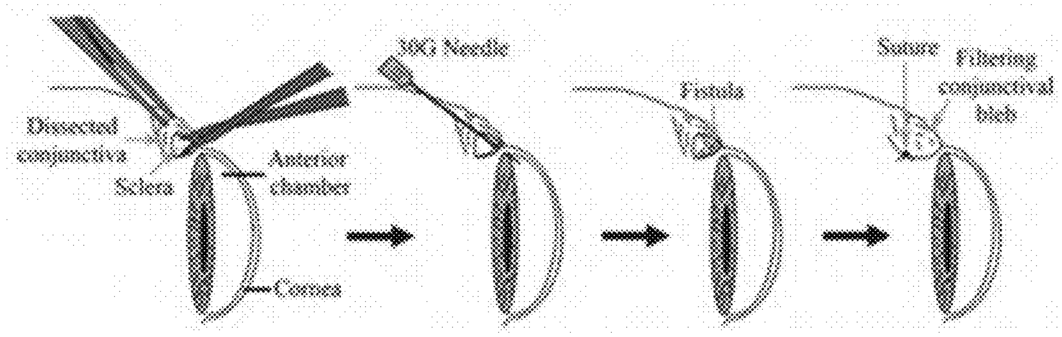
FIG. 1 shows a mouse model of conjunctival scarring.

As explained above, there is a need for an improved outcome of glaucoma surgery. In general terms, the invention relates to an improved outcome of glaucoma surgery though restoration of normal conjunctival tissue architecture by using valproic acid. In particular, the present invention may protect the function of an ocular surface from adverse responses to the glaucoma surgery. The present invention also relates to the preservation of collagen architecture, which may in turn reduce the level of disorganization in the scar collagen being deposited and preserve normal vasculature, which may result in improved surgical outcome. Additionally, the present invention results in the reduction of the amount/concentration of anti-metabolite used during glaucoma surgery.

According to a first aspect, the present invention provides use of valproic acid (VPA) in the manufacture of a medicament for preventing tissue degeneration following glaucoma surgery.

The present invention also provides use of VPA in the manufacture of a medicament for maintaining a subconjunctival bleb formed in glaucoma surgery. In particular, the maintaining a subconjunctival bleb comprises maintaining conjunctival collagen architecture. The maintaining conjunctival collagen architecture may be as described below. For example, the bleb may be maintained by inhibiting conjunctival scarring. Scarring may lead to failure of a bleb and thereby sustain an intraocular pressure (IOP) reduced by the glaucoma surgery.

VPA is known as a first-generation antiepileptic drug and has been used clinically for many years. VPA and its salts are widely prescribed for other neurological disorders including bipolar mania, migraines, etc. VPA has good efficacy and pharmacoeconomic profiles for neurological disorders, as well as a relatively favourable safety profile.

The VPA according to any aspect of the present invention may comprise any suitable form of VPA. According to a particular aspect, the VPA may comprise, but is not limited to, a VPA derivative, a VPA analog, a VPA salt, a VPA ester, or combinations thereof. For example, the VPA derivative may comprise but is not limited to, divalproex, 2-n-propyl-3-aminopentanoic acid, 2-π-propyl-4-aminopentanoic acid or a combination thereof. The VPA analog may comprise, but is not limited to, 2-n-propyl-4-hexynoic acid. The VPA salt may comprise, but is not limited to, sodium valproate, calcium valproate, valproate semisodium, and other valproate alkali and alkali earth salts, or a combination thereof. In particular, the VPA may comprise valproate sodium.

The VPA may have any suitable concentration. For example, the VPA may have a concentration of 100-1000 μg/mL. In particular, the VPA may have a concentration of 150-950 μg/mL, 200-900 μg/mL, 250-850 μg/mL, 300-800 μg/mL, 350-750 μg/mL, 400-700 μg/mL, 450-650 μg/mL, 500-600 μg/mL. Even more in particular, the VPA may have a concentration of 150-300 μg/mL.

The glaucoma surgery according to any aspect of the present invention may be any suitable glaucoma surgery. For example, the glaucoma surgery may comprise glaucoma filtering surgery or minimally invasive glaucoma surgery (MIGS). The glaucoma surgery may comprise ab externo glaucoma surgery or ab interno glaucoma surgery. In particular, the glaucoma surgery may comprise creating a subconjunctival space or bleb. The subconjunctival space/bleb may serve as a reservoir for aqueous humour.

According to a particular aspect, the glaucoma surgery may be MIGS and may comprise implanting a glaucoma tube shunt under a subconjunctival space. In particular, the glaucoma surgery may be ab externo glaucoma surgery and may comprise, but is not limited to, glaucoma filtration surgery, or implanting a glaucoma tube shunt under a subconjunctival space. The glaucoma tube may be any suitable glaucoma tube known in the art. In particular, the glaucoma tube may be PRESERFLO® MicroShunt (formerly known "InnFocus MicroShunt"). PRESERFLO® MicroShunt is an implantable glaucoma drainage device made of an extremely flexible SIBS [poly(Styrene-block-IsoButylene-block-Styrene)] polymer with a tube of 350 μm outer diameter and a lumen of 70 μm. It has triangular fins that prevent migration of the tube into the anterior chamber. The device may be designed to be implanted under the subconjunctival/Tenon space. The PRESERFLO® MicroShunt is manufactured and provided by InnFocus, Inc.

Ab interno glaucoma surgery may comprise a surgery for implanting a glaucoma stent under the subconjunctival space from cornea. The glaucoma stent may be any suitable glaucoma stent known in the art. In particular, the glaucoma stent may be Allergan's Xen Gel Stent.

According to a particular aspect, the glaucoma surgery may comprise use of an anti-metabolite. The anti-metabolite may be any suitable anti-metabolite for use in glaucoma surgery. In particular, the anti-metabolite may be used intraoperatively during glaucoma surgery. The anti-metabolite may comprise, but is not limited to, mitomycin C (MMC), 5-fluorouracil (5FU), or a combination thereof. According to a particular aspect, the anti-metabolite may be MMC.

The anti-metabolite used in the glaucoma surgery may have a suitable concentration. For example, the concentration of the anti-metabolite as used in the glaucoma surgery may be <1.0 mg/mL. In particular, the concentration of the anti-metabolite may be ≤0.9 mg/mL, ≤0.5 mg/mL, ≤0.4 mg/mL, ≤0.2 mg/L, ≤0.1 mg/L. Even more in particular, the concentration of the anti-metabolite may be ≤0.1 mg/mL.

The medicament and/or the VPA may be in any suitable form. For example, the medicament and/or the VPA may be suitable for ophthalmic administration. In particular, the medicament and/or the VPA may be suitable for subconjunctival, intravitreal, or topical administration. The medicament and/or the VPA may be configured for administration by a wide variety of ophthalmic delivery routes, such as subconjunctival injection, or other ocular delivery routes and/or forms of administration known in the art. The medicament or VPA may be prepared in liquid form, such as for administration via eye drops, or may be in dried powder form, such as lyophilized form.

The medicament may be suitable for any appropriate dosage regimen. Accordingly, the medicament may be suitable for administration at any suitable time. The dosage regimen may be based on various factors such as the age, condition, body weight, sex, and diet of the subject, the severity of the condition, and other clinical factors.

According to a particular aspect, the medicament may be suitable for administration immediately following the glaucoma surgery. For example, a single dose of the medicament may be provided immediately following the surgical event. In addition to a single dose, further repeated doses of the medicament may be provided. In particular, in addition to a single dose, daily, weekly, bi-weekly, monthly, and bi-monthly doses of the medicament may be provided. The medicament may be suitable for repeated administration for up to years following the glaucoma surgery. In particular, the medicament may be suitable for repeated administration for 1-120 months, 2-96 months, 3-72 months, 4-60 months, 5-48 months, 6-36 months, 8-24 months, 12-18 months following the glaucoma surgery. Even more in particular, the medicament may be suitable for repeated administration for up to 4 months following the glaucoma surgery.

According to a particular aspect, the medicament may be suitable for administration daily for up to 6 months, 4 months, 3 months, 2 months, 1 month, 3 weeks, 2 weeks, 1 week following the glaucoma surgery. In particular, the medicament may be suitable for administration daily for up to 12 weeks following the glaucoma surgery.

According to a particular aspect, the preventing tissue degeneration may comprise maintaining conjunctival collagen architecture. For the purposes of the present invention, maintaining conjunctival collagen architecture may be defined as reduction of collagen fiber thickness by about 25% and/or reduction of collagen reticulation by about 30%.

In particular, the maintaining conjunctival collagen architecture comprises suppression of alterations in collagen architecture and maintenance of the integrity of the conjunctival vasculature. Even more in particular, the maintaining conjunctival collagen architecture comprises a reduction in the average thickness of collagen fibers formed following the glaucoma surgery. The maintaining may further comprise an inhibition in reticulation of collagen. In particular, the maintaining may comprise an inhibition in reticulation of collagen by 30%. The maintaining may further comprise enhanced expression of Vegfa.

Since the VPA is able to prevent perturbation of collagen architecture during wound healing following glaucoma surgery by a reduction in collagen fiber thickness and collagen reticulation, the conjunctival architecture may be preserved, thereby maintaining the biomechanical properties of the conjunctiva and its role in supporting blood and lymphatic vasculatures. In view of the preservation of the conjunctival architecture, the conjunctiva may also be able to act as a protective barrier against infection following glaucoma surgery.

Further, the use of VPA enables a reduced concentration of anti-metabolite to be used intraoperatively during the glaucoma surgery. This enables the toxic effects of anti-metabolites on the conjunctival tissues to be significantly reduced, thereby preserving the health of conjunctival tissues.

The present invention, according to a third aspect, provides use of valproic acid (VPA) in the manufacture of a medicament for forming a weak subconjunctival scar following glaucoma surgery.

The glaucoma surgery may be as defined above. In particular, the glaucoma surgery may comprise implanting a glaucoma tube shunt under a subconjunctival space.

According to a particular aspect, the forming a weak subconjunctival scar may comprise preventing encapsulation of the glaucoma tube shunt by collagen fibers. According to another particular aspect, the forming a weak subconjunctival scar may enable the glaucoma tube shunt to maintain its aqueous outflow ability through a lumen thereof. In particular, the medicament may be suitable for administration to a subject to thereby lead to development of a weaker subconjunctival scar through the presence of smaller (reduced collagen content) and thinner collagen fibers resulting in a favourable bleb morphology that would facilitate aqueous outflow and maintain the functioning of the microshunt.

The glaucoma surgery may comprise use of an anti-metabolite. The anti-metabolite may be any suitable anti-metabolite. For example, the anti-metabolite may be, but not limited to, mitomycin C (MMC), 5-fluorouracil (5FU), or a combination thereof. The anti-metabolite may have a suitable concentration. According to a particular aspect, the anti-metabolite may have a concentration of ≤1.0 mg/mL. In particular, when combined with low dose anti-metabolite, the combination of VPA and anti-metabolite may additionally reduce collagen fiber length, thereby making the subconjunctival scar formed even weaker.

There is also provided a use of VPA in the manufacture of a medicament for preventing encapsulation of a glaucoma tube shunt implanted under a subconjunctival space.

Another aspect of the present invention is a use of VPA in the manufacture of a medicament for maintaining aqueous outflow ability of a glaucoma tube through a lumen thereof after the tube is implanted under a subconjunctival space.

According to a further aspect, the present invention provides a method of preventing tissue degeneration following glaucoma surgery, comprising administering an effective amount of VPA.

According to a further aspect, there is provided a method of maintaining subconjunctival bleb formed in glaucoma surgery, comprising administering an effective amount of VPA.

The present invention also provides a method of forming a weak subconjunctival scar following glaucoma surgery, comprising administering an effective amount of VPA. The glaucoma surgery may be as defined above. In particular, the glaucoma surgery may comprise implanting a glaucoma tube shunt under a subconjunctival space.

In particular, the forming a weak subconjunctival scar may comprise preventing encapsulation of the glaucoma tube shunt by collagen fibers. According to another particular aspect, the forming a weak subconjunctival scar may enable the glaucoma tube shunt to maintain its aqueous outflow ability through a lumen thereof.

According to a particular aspect, the medicament may further comprise an anti-metabolite. In particular, the anti-metabolite may be as described above.

There is also provided use of VPA in the manufacture of an adjunct to glaucoma surgery. The adjunct may sustain an IOP reduced by the glaucoma surgery. In particular, the VPA may be used as an adjunct to glaucoma surgery.

The VPA and glaucoma surgery, as well as anti-metabolite, may be as described above.

The present invention also provides a method of preventing tissue degeneration following glaucoma surgery comprising administering VPA to a patient in need thereof.

There is also provided a method of maintaining a subconjunctival bleb formed in glaucoma surgery comprising administering VPA to a patient in need thereof.

The present invention also provides a method of forming a weak subconjunctival scar following glaucoma surgery comprising administering VPA to a patient in need thereof. A method of preventing encapsulation of a glaucoma tube shunt implanted under a subconjunctival space comprising administering VPA to a patient in need thereof is also provided.

The present invention also provides a method of maintaining aqueous outflow ability of a glaucoma tube through a lumen thereof after the tube is implanted under a subconjunctival space comprising administering VPA to a patient in need thereof.

The glaucoma surgery may be as described above. The VPA may be as described above.

There is also provided VPA for use in preventing tissue degeneration following glaucoma surgery. Another aspect of the present invention is VPA for use in maintaining a subconjunctival bleb formed in glaucoma surgery. The present invention also provides VPA for use in forming a weak subconjunctival scar following glaucoma surgery.

Another aspect of the present invention is VPA for use in preventing encapsulation of a glaucoma tube shunt implanted under a subconjunctival space. Yet another aspect of the present invention is VPA for use in maintaining aqueous outflow ability of a glaucoma tube through a lumen thereof after the tube is implanted under a subconjunctival space.

The glaucoma surgery may be as described above. The VPA may be as described above.

The present invention also provides an agent for preventing tissue degeneration following glaucoma surgery, wherein the agent comprises VPA. Another aspect of the present invention is an agent for maintaining a subconjunctival bleb formed in glaucoma surgery, wherein the agent comprises VPA.

There is also provided an agent for forming a weak subconjunctival scar following glaucoma surgery, wherein the agent comprises VPA.

Another aspect of the present invention is an agent for: preventing encapsulation of a glaucoma tube shunt implanted under a subconjunctival space; and/or maintaining aqueous outflow ability of a glaucoma tube through a lumen thereof after the tube is implanted under a subconjunctival space, wherein the agent comprises VPA.

The glaucoma surgery may be as described above. The VPA may be as described above.

Having now generally described the invention, the same will be more readily understood through reference to the following examples which are provided by way of illustration, and are not intended to be limiting.

EXAMPLE

Example 1—Mouse Model of Conjunctival Scarring

The mouse model of conjunctival scarring was performed as shown in FIG. 1. The conjunctiva was dissected to reveal the sclera where an incision was made into the anterior chamber. The resulting fistula allowed aqueous humor to exit into and underneath the conjunctiva. The accumulated fluid underneath the sutured conjunctiva was observed as a conjunctival bleb.

The mouse model of conjunctival scarring was validated using MMC. The mouse demonstrated a similar response to humans who have undergone glaucoma surgery when MMC was applied in exactly the same manner.

To determine whether VPA has the capacity to protect collagen architecture, quantitative multiphoton imaging as described in Xu S et al (*J. Hepatol.,* 2014, 61(2):260-269) was used to measure collagen properties in the mouse model of conjunctival scarring treated with VPA. The onset of scarring, as indicated by peak production of collagen mRNA, was measured on day 7 post-surgery. The mature scar was measured on day 14 post-surgery when collagen mRNA production was subdued.

Figure 2:
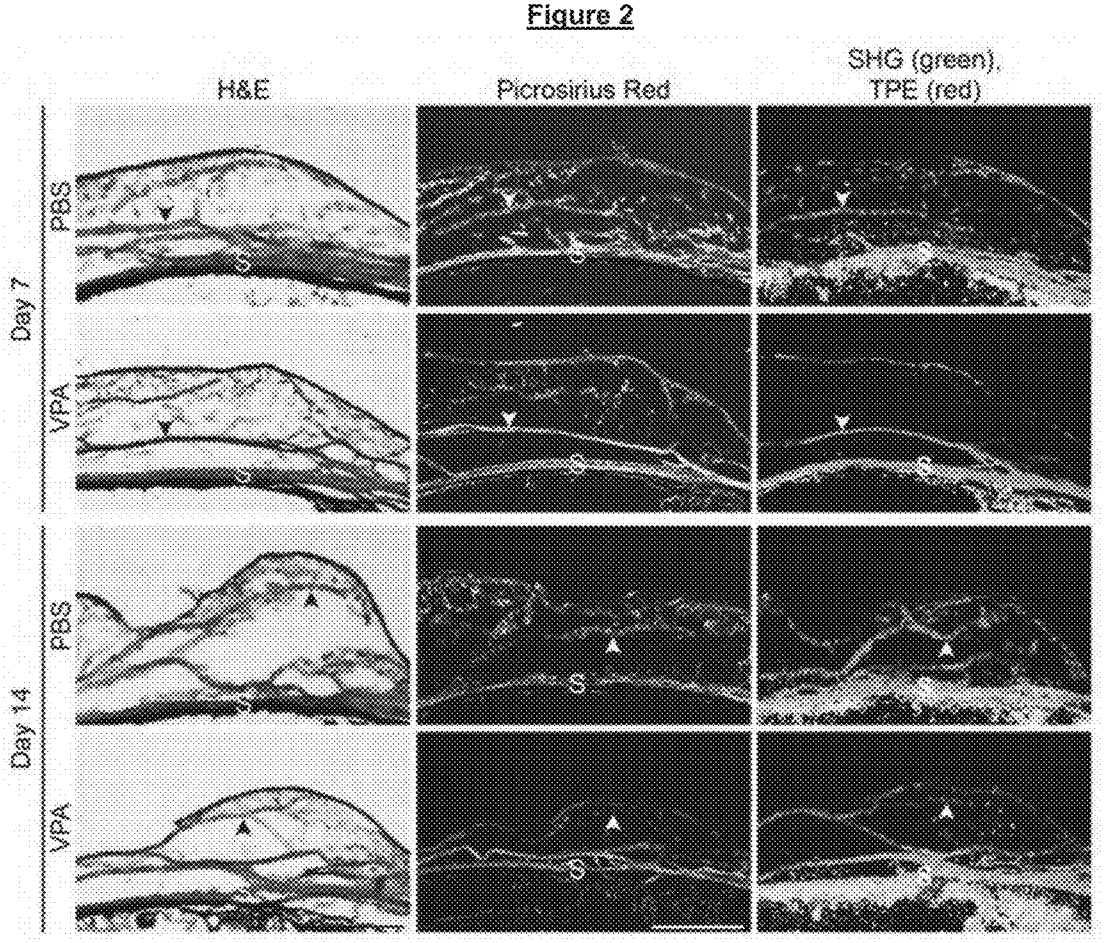
FIG. 2 shows a visualization of phosphate buffered saline (PBS) and VPA-treated collagen architecture in the mouse model of operated conjunctiva by hematoxylin and eosin (H&E) staining, picrosirius red staining and Second Harmonic Generation (SHG) at the indicated time points post-surgery.

To study the impact of VPA on the collagen architecture during the onset of scarring on day 7, mice were injected with 300 μg/ml VPA directly into the operated area immediately after surgery and on day 2. To determine the effect of VPA in the mature scar on day 14, mice were injected as above, with an additional injection on day 7. By this method, it could be readily observed in histologically-stained sections as well as multiphoton scans that collagen fibers in the VPA-treated eyes were thinner than those in the PBS-treated control eyes. Exemplary collagen fibers showing the thinning effect of VPA are indicated by the white arrowheads in FIG. 2.

Figure 3:
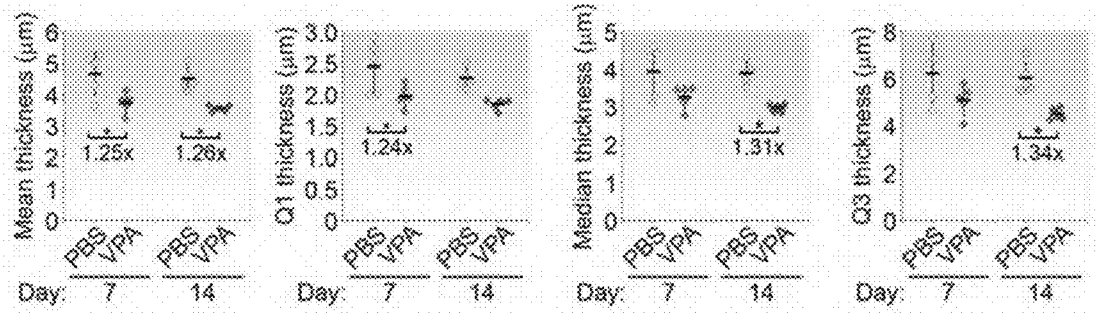
FIG. 3 shows reduction of collagen fiber thickness in VPA-treated post-operative conjunctiva of the mouse model.

Quantitative multiphoton analyses of the operated conjunctival sections, verified that collagen thickness was indeed reduced in the VPA-treated tissues (FIG. 3). The entire range of thin, median and thick collagen fibers in the VPA-treated conjunctivas were all comparatively thinner than those in PBS-treated counterparts.

Figure 4:
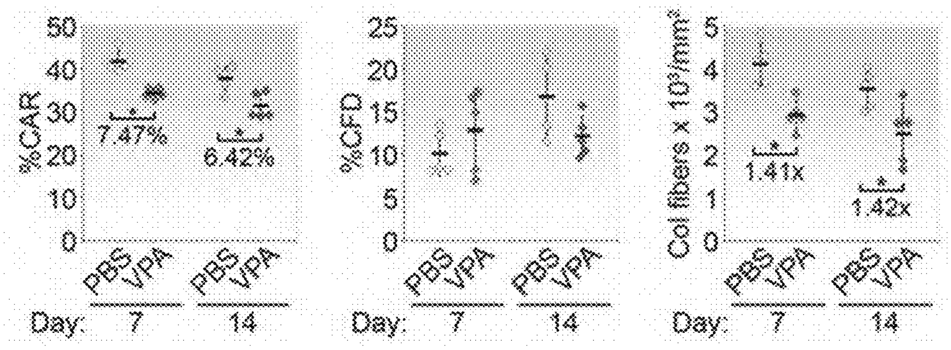
FIG. 4 shows reduction of collagen fiber intensity in the VPA-treated post-operative conjunctiva of the mouse model, measured by collagen area ratio (CAR), collagen fiber density (CFD) and number of collagen fibers per $mm^2$.

Quantitative analyses of collagen intensity (FIG. 4) also corroborated that VPA reduced collagen production in the mouse model of conjunctival scarring. Although the number of fibers were diminished in the VPA-treated tissues, the packing density was not significantly different to PBS controls. Collagen intensity measured as collagen area ratio (CAR) was significantly reduced in both days 7 and 14 VPA-treated tissues. The lack of significant difference in collagen fiber density (CFD) upon VPA treatment indicated that the collagen fibers were not packed differently from PBS controls. In agreement with the capacity of VPA to reduce the quantity of collagen induced after surgery, the number of collagen fibers per $mm^2$ was significantly reduced in the operated tissues at both time points.

Figure 5:
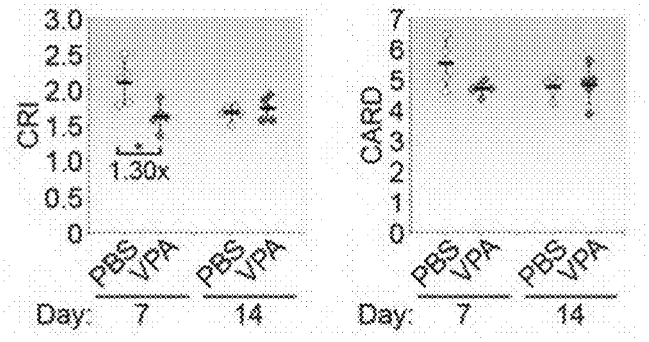
FIG. 5 shows that collagen fiber reticulation was not induced in VPA-treated post-operative conjunctiva of the mouse model, where collagen structure is measured by Collagen Reticulation Index (CRI) and collagen area reticulation density (CARD)

Most importantly, multiphoton analyses measured a facet of collagen architecture that was not readily visualized by eye. Whereas PBS treatment increased collagen reticulation (or branching), VPA treatment inhibited this phenomenon, as shown by the significant reduction in Collagen Reticulation Index (CRI) when compared to PBS treatment on day 7 (FIG. 5). VPA activity in suppressing the increase in CRI on day 7 has important implications since this is the time point for peak collagen induction in the wounded tissue. The implication is that VPA can act to prevent overt tissue structural changes in the event of excessive and potentially extended wound healing, both of which are associated with pathological scarring. As CRI in the day 14 mature scar is similar to unoperated tissue, the lack of effect of VPA in the day 14 mature scar is also important as it suggests that VPA will not alter tissue structural integrity in normal tissue, but will affect excessive scarring exclusively. Collagen reticulation was not induced in VPA-treated post-operative conjunctiva after experimental surgery. Collagen structure was measured as CRI and collagen area reticulation density (CARD).

These data, measured at the micron scale, indicate that VPA treatment prevents perturbation of collagen architecture in terms of collagen fiber thickness and collagen reticulation, in addition to its capacity to reduce collagen fiber intensity. Hence, VPA treatment may be a method for preserving the conjunctival architecture which is important for the maintenance of its biomechanical properties and its role in supporting the blood and lymphatic vasculatures.

Example 2—Rabbit Model of Microshunt Implant Surgery and Human Microshunt Implant Surgery For application in the rabbit model of microshunt implant surgery (PRESERFLO® MicroShunt, Santen), the dosage of VPA to be used was determined using primary rabbit conjunctival fibroblasts for (1) effectiveness in reducing type I collagen, and (2) non-toxicity on cell growth, as shown in FIG. 6. The data indicated that 300 μg/ml VPA is the lowest concentration that is effective in significantly reducing Col1a1 expression in rabbit conjunctival fibroblasts without disrupting cell proliferation.

Figure 6A:
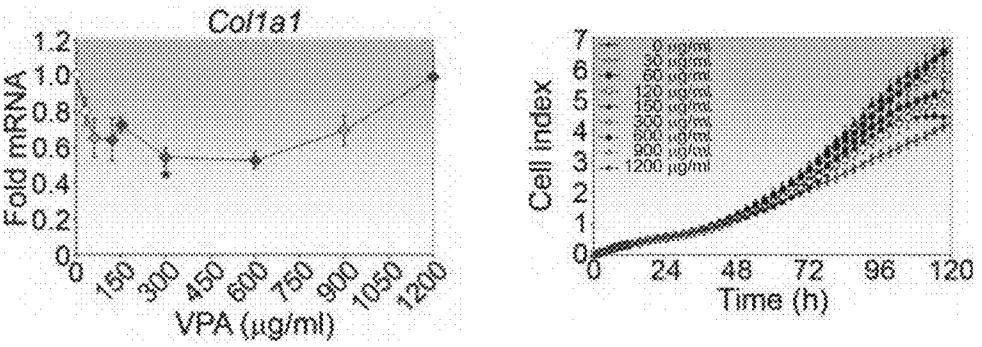
FIG. 6A shows that VPA inhibits steady-state type I collagen expression in primary rabbit conjunctival fibroblasts and FIG. 6B shows that VPA inhibits steady-state type I collagen expression in human Tenons conjunctival fibroblasts.

As seen from FIG. 6A, VPA inhibits steady-state type I collagen expression in primary rabbit conjunctival fibroblasts.

Figure 6B:
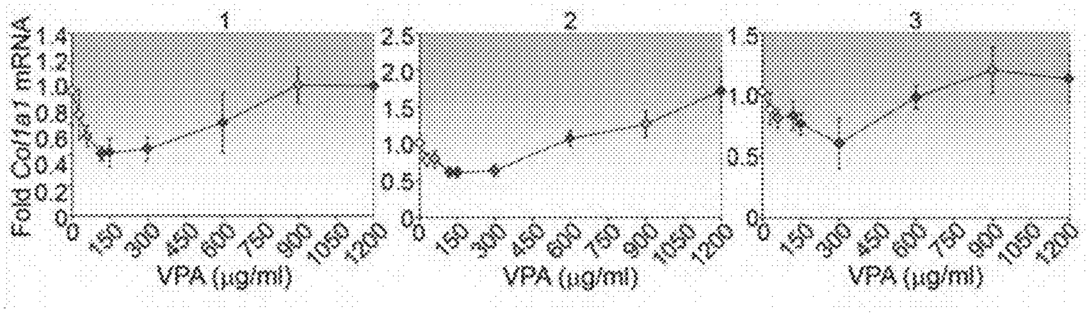

Likewise, for application in human, the dosage of VPA to be used was determined as in the rabbit model for effectiveness in reducing type I collagen. The effect of VPA on type I collagen expression in human Tenons conjunctival fibroblasts derived from three independent donors was investigated, and the results are as shown in FIG. 6B. It can be seen that like the rabbit model, 300 μg/ml VPA is the lowest concentration that is effective in significantly reducing Col1a1 expression without disrupting cell proliferation.

Example 3—Efficacy of VPA in the Rabbit Model of Microshunt Implant Surgery

Figure 7:
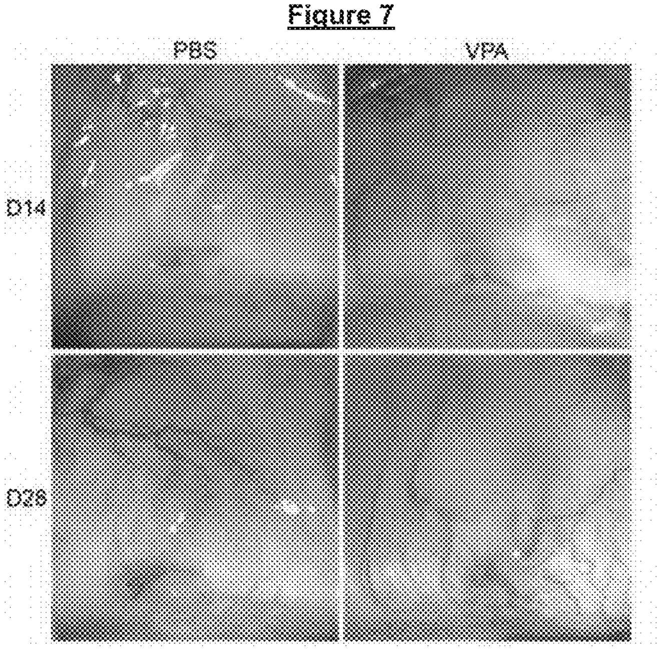
FIG. 7 shows the effectiveness of VPA in maintaining the microshunt implant in the rabbit model for at least 28 days post-surgery, as compared to PBS.

The rabbit model of microshunt implant surgery using the PRESERFLO® MicroShunt (Santen) was performed with a total of 11 injections of 300 μg/ml VPA, immediately after surgery, and once daily for first 7 days, followed by injections on days 10, 14 and 21 post-surgery. The rabbit eyes were evaluated by slit lamp photography (FIG. 7). As can be seen, whereas the PBS treated bleb has already failed by day 14, VPA was effective in maintaining a filtering bleb for at least 28 days.

Confocal microscopy was used to correlate bleb appearance and function. It is known that significant positively correlating features include cyst size and vasculature density/tortuosity.

Figure 8:
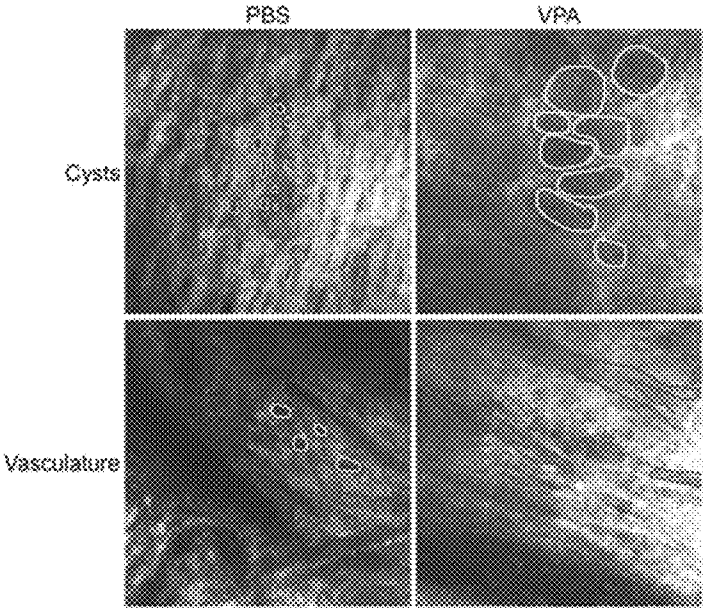
FIG. 8 shows the development of cysts and maintenance of vasculature structure in the bleb of the rabbit model treated with PBS and VPA, imaged by confocal microscopy, 28 days post-surgery.

In this example, the PBS-treated bleb featured smaller cysts in a background of tightly-packed collagen fibers and amorphous-looking tissue (FIG. 8). Notably, the vasculature appeared tortuous. In contrast, the VPA-treated bleb was characterized by large cysts amid loosely packed collagen fibers which were more regularly arranged and less amorphous. Markedly, the vasculature was straight in the VPA-treated conjunctiva. These observations support the capacity of VPA to preserve the structure of the conjunctival vasculature, and in combination with the development of large cysts, may contribute to improved bleb function and survival.

Figure 9:
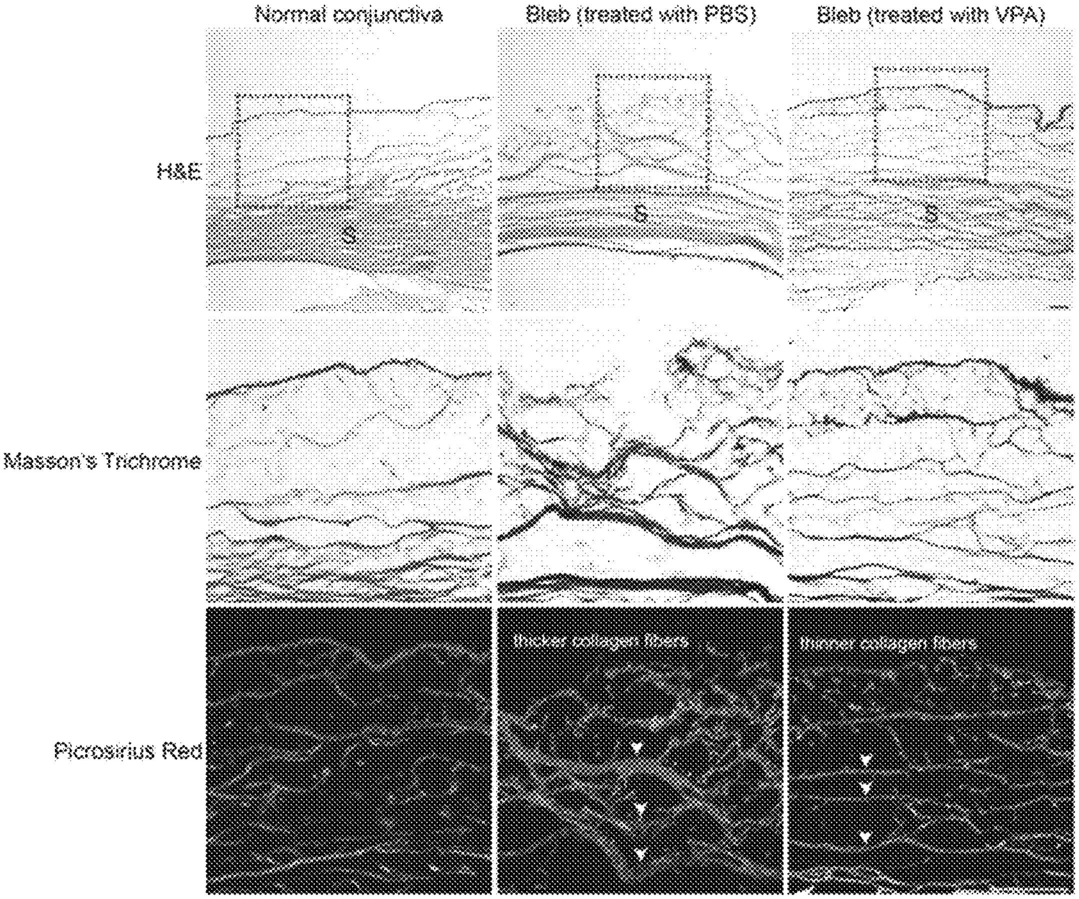
FIG. 9 shows a histological visualization of collagen characteristics in the rabbit model of microshunt implant surgery treated with VPA, 28 days post-surgery.

The capacity of VPA to maintain the collagen architecture of the conjunctiva was verified by histological analyses. When examined against normal, unoperated conjunctiva, the PBS-treated bleb featured thick and disorganized collagen fibers (FIG. 9). In contrast, the VPA-treated bleb was characterized by thinner and similarly organized array of collagen fibers when compared to the normal tissue (FIG. 9). These data suggest that treatment with VPA will maintain the collagen structure of the conjunctiva when fitted with an eluting implant. VPA may therefore preserve the biomechanical/scaffolding property and protective barrier role of the conjunctiva. By preventing structurally degenerative responses in the conjunctiva, VPA may therefore increase the success of the surgery.

Figure 10:
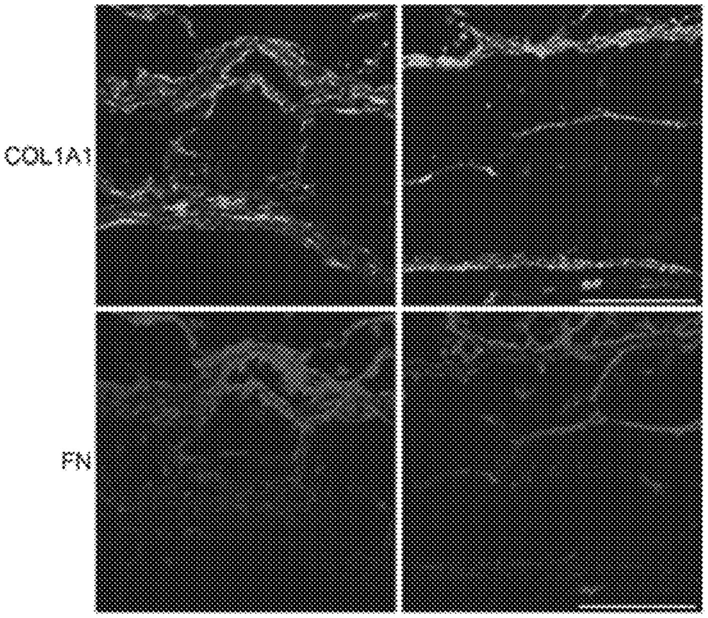
FIG. 10 shows an immunofluorescent visualization of collagen and fibronectin characteristics in the rabbit model of microshunt implant surgery treated with VPA, 28 days post-surgery.

Differential collagen structures due to VPA and PBS control treatments were further visualized by immunofluorescent staining of the conjunctival cryosections. Antibodies specific for type I collagen (COL1A1) and fibronectin (FN) confirmed the development of thicker collagen and fibronectin fibers in the PBS-treated conjunctiva (FIG. 10). In contrast, the VPA-treated bleb was permeated by thinner and more diffusely distributed fibers of both proteins (FIG. 10). These data suggest that VPA affected not only collagen distribution and structure, but also that of other extracellular matrix proteins such as fibronectin. Fibronectin is involved in wound contraction during wound healing, amongst other functions. By preventing the formation of excessive or thick fibronectin fibers, VPA may deter pathological collagen contractures from developing in the wounded conjunctiva.

Figure 11:
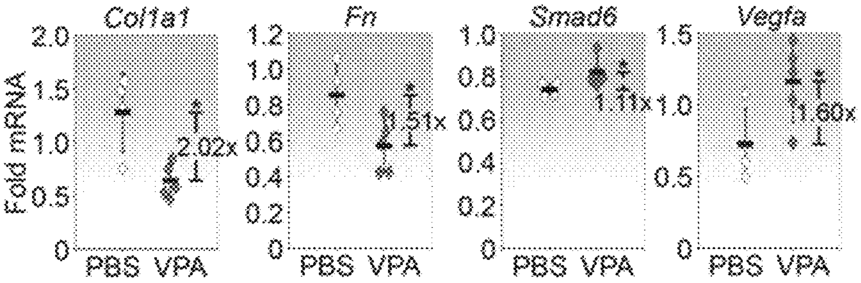
FIG. 11 shows expression of profibrotic and proangiogenic transcripts in the rabbit model of microshunt implant surgery treated with VPA.

The reduction in thickness of collagen and fibronectin fibers suggests that less collagen and fibronectin may be produced upon VPA treatment. This was verified by analysing the quantity of collagen and fibronectin transcripts in the treated rabbit conjunctivas. As shown in FIG. 11, the expression of both these genes in the day 28 rabbit tissues were significantly reduced upon VPA treatment when compared with PBS controls. It was also verified that Smad6 was significantly induced with VPA treatment, corroborating the previous finding from the mouse model of conjunctival scarring that alteration of Smad6 expression is a mechanism for Col1a1 downregulation by VPA. Surprisingly, the expression of Vegfa, the archetypal growth factor for angiogenesis, was significantly elevated in the tissue treated with VPA. This finding is in line with the capacity of VPA to preserve the vasculature in the operated tissue which may be inhibited by the development of a denser and disorganized collagen scaffold in the PBS control visualized by confocal microscopy.

In summary, the rabbit model of microshunt surgery implant indicated that VPA treatment retained the tissue/collagen architecture as well as the vasculature of the operated tissue and may therefore be used to preserve the essential functions of the normal conjunctiva. In other words, by reducing degenerative responses to the surgery, and simultaneously allowing the development of large cysts, VPA may therefore reduce adverse effects in the aftermath of surgery while improving bleb function and serve to be beneficial as an adjunct for use with the PRESERFLO® MicroShunt.

Example 4—Efficacy of VPA to Reduce MMC Exposure in the Rabbit Model of Microshunt Implant Surgery The rabbit model of microshunt implant surgery using the PRESERFLO® MicroShunt (Santen) was performed and treated under these conditions:

(a) 0.4 mg/ml MMC via sponge for 1 min;
(b) 0.1 mg/ml MMC via sponge for 1 min; and
(c) 0.1 mg/ml MMC via sponge for 1 min in combination with a total of 11 injections of 300 μg/ml VPA, immediately after surgery, and once daily for first 7 days, followed by injections on days 10, 14 and 21 post-surgery.

Figure 12:
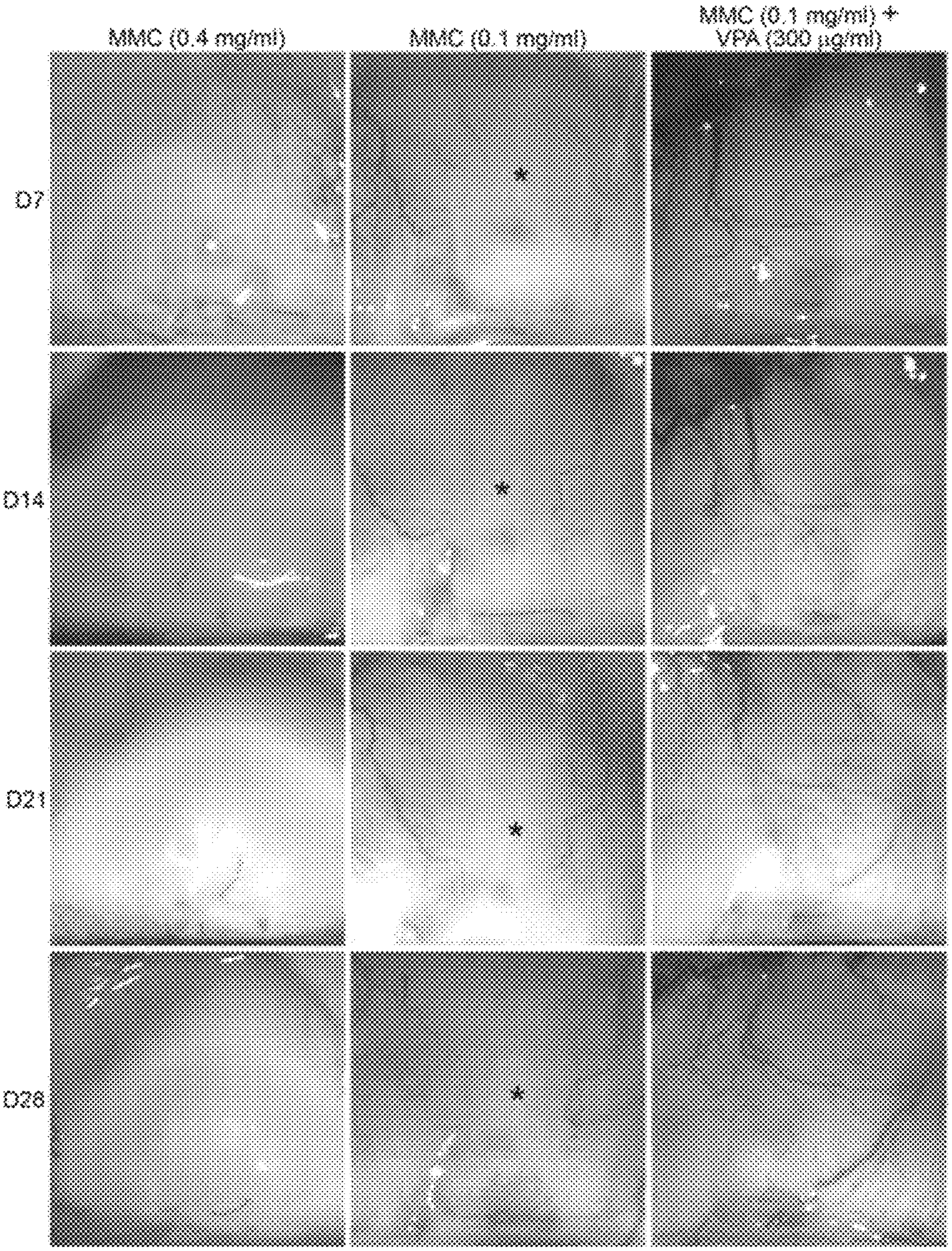
FIG. 12 shows improved bleb morphology in the rabbit model of microshunt implant surgery when VPA is used in combination with low dose MMC.

The rabbit eyes were evaluated by slit lamp photography (FIG. 12). As can be seen, all the blebs appeared to be functional by day 28. However, the morphologies of the blebs differed greatly amongst the treatment conditions.

Standard MMC treatment at 0.4 mg/ml resulted in a starkly avascular and cystic bleb. The treated area was clearly demarcated from the normal conjunctiva. Given that the vasculature is a purveyor of oxygen and nutrients, and also provides the immune response to potential infection, treatment with MMC at 0.4 mg/ml exposed the treated area to high risk of tissue degeneration and increased vulnerability to infection.

MMC treatment at 0.1 mg/ml resulted in a less avascular and mildly cystic bleb compared to treatment with 0.4 mg/ml MMC although a small avascular area in the treated area (marked by *, FIG. 12) remained obvious up to 28 days. The risk of tissue degeneration and infection was therefore much reduced in this bleb when MMC concentration was reduced.

MMC at 0.1 mg/ml in combination with VPA resulted in a diffuse bleb and normal vascularization penetrating the entire treated area. The treated area, resembling much like normal conjunctival tissue, was expected to be at the lowest risk of tissue degeneration and infection.

Figure 13:
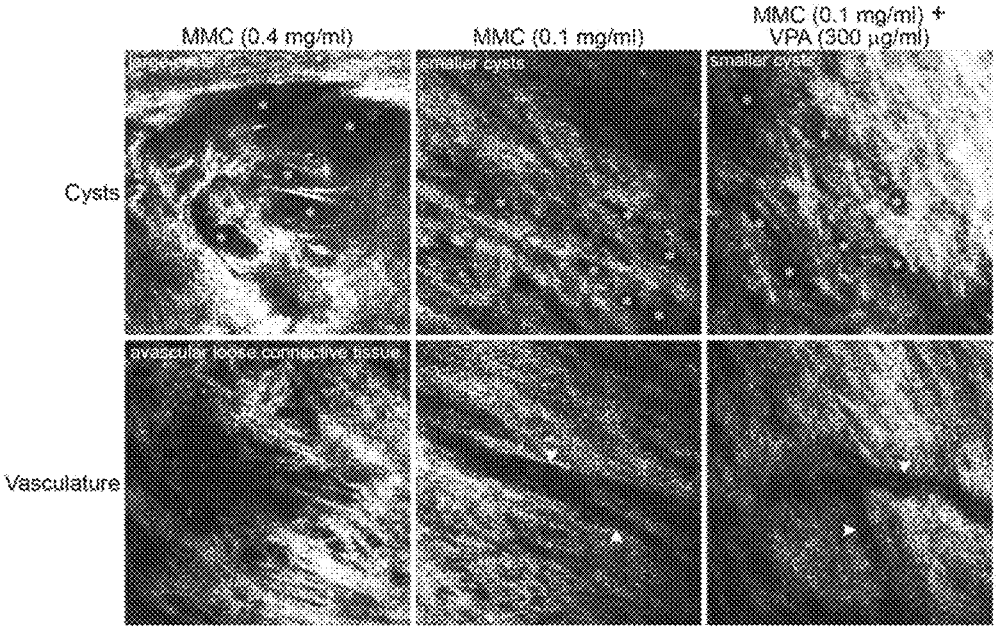
FIG. 13 shows maintained vasculature in the bleb of the rabbit model, 28 days post-surgery, when lower dose of MMC is used.

Confocal microscopy revealed that standard treatment with 0.4 mg/ml MMC resulted in large cysts (marked by *, FIG. 13) in a background of loose collagen fibers. The vasculature was not detectable. In contrast, the blebs treated by 0.1 mg/ml MMC alone or in combination with VPA were characterized by smaller cysts (marked by *, FIG. 13). Under the latter two conditions, any differences that may exist in the collagen matrix cannot be discerned but the vasculature may be easily visualized (arrowheads, FIG. 13). These observations confirm that MMC at high dose allows the formation of large cysts that contribute to bleb function. A lower dose of MMC resulted in smaller cysts whose sizes did not perceptively increase even upon treatment with VPA. However, the retaining presence of the vasculature is imperative for conjunctival health.

Figure 14:
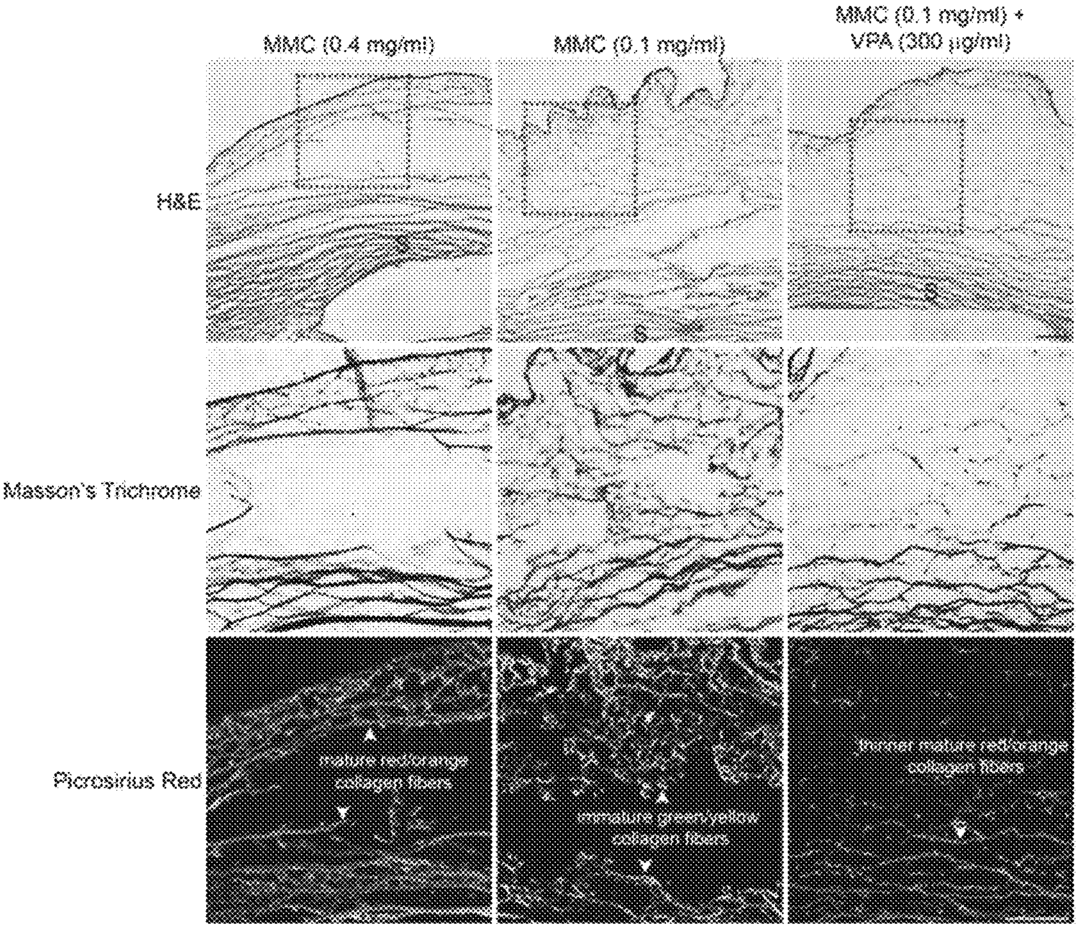
FIG. 14 shows a histological visualization of collagen characteristics in the rabbit model of microshunt implant surgery, 28 days post-surgery, treated with high and low doses of MMC and in combination with VPA.

The finer capacity of VPA to maintain the collagen architecture of the conjunctiva is most clearly demonstrated by histological analyses. Treatment with standard 0.4 mg/ml MMC resulted in a gaping space in the bleb matrix where collagen fibers were obliterated (FIG. 14). The collagen fibers that remained were mature fibers, presumably survivors from the pre-operative tissue. In contrast, at the lower 0.1 mg/ml MMC dose, numerous immature and disorganized collagen fibers may be detected (arrowheads, FIG. 14), suggesting the continuous production of collagen up to and beyond day 28 in the operated area. When the lower dose MMC was applied in conjunction with VPA, the collagen network was sparse and composed of mainly mature fibers (FIG. 14). This striking histology suggests that while there was collagen production in the postoperative period, VPA inhibited the production of new fibers at some point before day 28 so that the matrix examined consisted mainly of greatly reduced and thinner, mature collagen fibers (arrowheads, FIG. 14). Overall, these data show that co-treatment with VPA allows a lower dose of MMC to be used that preserves the vasculature and achieves a collagen matrix that is closer to the normal tissue while maintaining efficacy of the microshunt in terms of bleb functioning and integrity.

Figure 15:
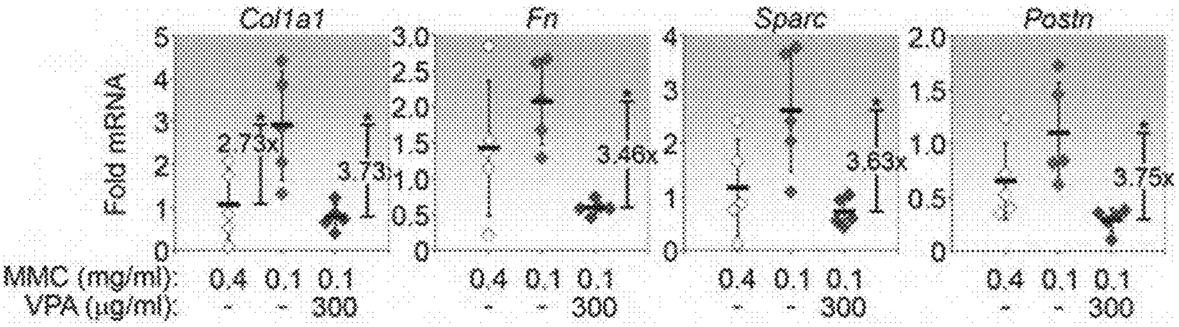
FIG. 15 shows expression of profibrotic and proangiogenic transcripts in the rabbit model of microshunt implant surgery, 29 days post-surgery, treated with high and low doses of MMC and in combination with VPA.

The differential histologies of the extracellular matrix may be reflected in differences in gene expression caused by the treatment conditions. This was verified by analysing the quantity of transcripts in the treated rabbit conjunctivas. As shown in FIG. 15, in which each symbol represents one rabbit eye (n=5 all conditions), the mRNA expression of Col1a1 in the day 28 rabbit tissues treated with 0.1 mg/ml MMC was significantly higher than both 0.4 mg/ml MMC or 0.1 mg/ml MMC+VPA treatments, corroborating the histological observations. Importantly, the level of Col1a1 transcript expression was similar between 0.4 mg/ml MMC and 0.1 mg/ml MMC+VPA treatments, indicating that the latter can replace the use of high MMC dose in causing a similar reduction in collagen production. Other fibrosis-associated genes including fibronectin, SPARC, and periostin gene expression were also significantly reduced with VPA co-treatment. Smad6 expression was not altered similarly as VPA alone, likely due to drug interactions with MMC.

Figure 16:
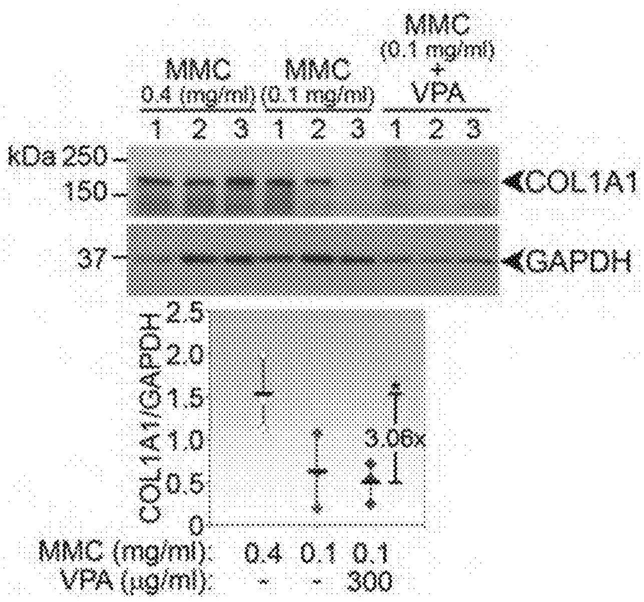
FIG. 16 shows protein expression of COL1A1 in the rabbit model of microshunt implant surgery, 29 days post-surgery, treated with high and low doses of MMC and in combination with VPA.

The mRNA data was verified with immunoblotting for COL1A1 production in the rabbit tissues. As can be seen in FIG. 16, in which each symbol represents one rabbit eye (n=5 all conditions), operated conjunctival levels of COL1A1 protein was lowest in tissues treated with the low MMC supplemented with VPA. This data may coincide with the histological evidence, where the collagen content measured in the tissue treated with 0.4 mg/mL MMC likely represented collagen that remained without further alterations following treatment since the tissue was metabolically inactive. In the case of the lower dose of 0.1 mg/ml MMC, where the treated tissues appeared to be comparatively active by displaying significantly higher levels of Col1a1 transcription (FIG. 15), and featuring the appearance of apparently newly-formed immature collagen fibers (FIG. 14), the deposited collagen content was similar to high MMC dose. Notably, when co-treated with VPA, the level of COL1A1 was reduced more consistently between independent rabbits, resulting in a significant mean 2.4-fold reduction when compared to treatment with 0.1 mg/ml MMC alone. This finding suggests that co-therapy with VPA not only maintains the tissue morphology, but also ensures greater consistency in maintaining the reduced COL1A1 levels compared to treatment with low dose MMC alone.

In summary, VPA preserved the conjunctival collagen architecture in both the mouse model of conjunctiva scarring and rabbit model of PRESERFLO® MicroShunt implant surgery. This strongly supports the capacity of VPA to maintain the biomechanical integrity of the conjunctiva following surgical implantation of the microshunt. Moreover, the maintenance of the conjunctival vasculature by VPA suggests that this drug may also sustain the general health of the tissue and uphold its role as a protective barrier against infection. Furthermore, the capacity of VPA to sustain goblet cell numbers in the operated conjunctiva indicates that this drug may be used pre- and pro-operatively to prevent the development of dry eye and improve glaucoma surgery outcome.

Example 5—Combination Therapy of VPA and Low Dose MMC for Reducing Post-Operative Scarring To investigate the effect of VPA on post-operative scarring, rabbit model of microshunt implant surgery as was performed and treated in Example 4 under conditions (a), (b) and (c) was repeated. The rabbit eyes were then evaluated.

Figure 17:
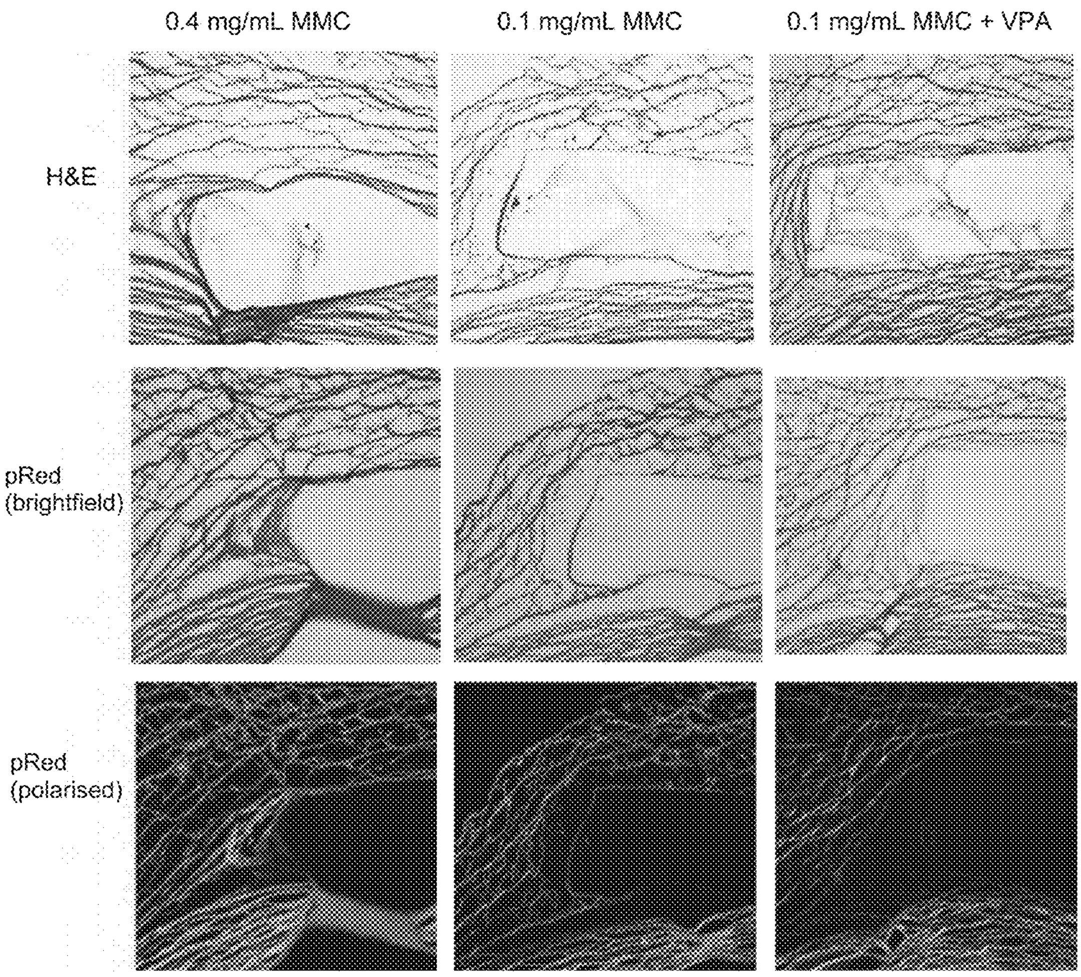
FIG. 17 shows histochemical visualisation of implant tip opening into the subconjunctival space in a rabbit model of MIGS treated with MMC or a combination of MMC and VPA.

FIG. 17 shows the histochemical visualization of the implant tip opening into the subconjunctival space in the rabbit model of MIGS treated as shown in the figure. Picrosirius red (pRed) stained sections viewed under polarised light revealed the presence of thick collagen fibers encapsulating the implant in the tissues treated with MMC alone, regardless of concentration used.

In contrast, treatment with VPA (300 μg/mL) reduced the presence of the thick fibers encapsulating the implant, particularly the tip. This shows that VPA treatment may reduce the risk of implant encapsulation and subsequent failure of the device.

Whilst the foregoing description has described exemplary embodiments, it will be understood by those skilled in the technology concerned that many variations may be made without departing from the present invention.

The invention claimed is:

1. A method of maintaining a subconjunctival bleb formed in minimally invasive glaucoma surgery (MIGS), comprising administering to a patient undergoing the MIGS an effective amount of valproic acid (VPA), wherein the MIGS comprises implanting a glaucoma tube shunt under a subconjunctival space and treating with mitomycin C (MMC) at a concentration of ≤0.1 mg/mL.

2. The method according to claim 1, wherein the VPA comprises a derivative, analog, salt, ester thereof, or combinations thereof.

3. The method according to claim 1, wherein the VPA has a concentration of 100-1000 μg/mL.

4. The method according to claim 1, wherein the administering is topical or subconjunctival.

5. The method according to claim 1, wherein the administering is immediately following the MIGS.

6. The method according to claim 1, wherein the administering is daily for at least 12 weeks following the MIGS.

7. The method according to claim 1, wherein the administering is repeated for up to 3-120 months following the MIGS.

8. A method of forming a weak subconjunctival scar following minimally invasive glaucoma surgery (MIGS) where a glaucoma tube shunt is implanted under a subconjunctival space, comprising administering to a patient in need thereof an effective amount of valproic acid (VPA) and mitomycin C (MMC) at a concentration of ≤0.1 mg/mL.

9. The method according to claim 8, wherein the forming a weak subconjunctival scar comprises preventing encapsulation of the glaucoma tube shunt by collagen fibers, or enables the glaucoma tube shunt to maintain its aqueous outflow ability through a lumen thereof.

10. A method of preventing encapsulation of a glaucoma tube shunt implanted under a subconjunctival space in a minimally invasive glaucoma surgery (MIGS); or maintaining aqueous outflow ability of a glaucoma tube through a lumen thereof after the tube is implanted under a subconjunctival space in a minimally invasive glaucoma surgery (MIGS), comprising administering to a patient in need thereof an effective amount of valproic acid (VPA) and mitomycin C (MMC) at a concentration of ≤0.1 mg/mL.

* * * * *